US007608392B2

(12) United States Patent
Rothel et al.

(10) Patent No.: US 7,608,392 B2
(45) Date of Patent: Oct. 27, 2009

(54) DIAGNOSTIC ASSAY FOR MEASURING A CELL MEDIATED IMMUNE RESPONSE (75) Inventors: James Stuart Rothel, Glen Huntly (AU); Steven Paul Wild, Kilsyth South (AU); Angela Cosgriff, Prahran (AU)

(73) Assignee: Cellestis Limited, South Melbourne, Victoria (AU)

( * ) Notice: Subject to any disclaimer, the term of this patent is extended or adjusted under 35 U.S.C. 154(b) by 215 days.

(21) Appl. No.: 10/477,571

(22) PCT Filed: Nov. 6, 2003

(86) PCT No.: PCT/AU03/01464

§ 371 (c)(1),
(2), (4) Date: Sep. 15, 2004

(87) PCT Pub. No.: WO2004/042396

PCT Pub. Date: May 21, 2004

(65) Prior Publication Data

US 2005/0014205 A1  Jan. 20, 2005

(30) Foreign Application Priority Data

Nov. 8, 2002   (AU) .............................. 2002952548

(51) Int. Cl.
G01N 33/53       (2006.01)
G01N 33/569      (2006.01)
(52) U.S. Cl. .................... 435/5; 435/7.24; 435/7.32; 435/7.94
(58) Field of Classification Search ...................... None
See application file for complete search history.

(56) References Cited

U.S. PATENT DOCUMENTS

| 5,128,270 | A | * | 7/1992 | Delacroix et al. | 436/518 |
| 5,334,504 | A | * | 8/1994 | Wood et al. | 435/7.32 |
| 5,494,799 | A | | 2/1996 | Wood et al. | |
| 5,707,819 | A | * | 1/1998 | Wood et al. | 435/7.32 |
| 5,877,273 | A | * | 3/1999 | Hance et al. | 530/300 |
| 5,885,529 | A | | 3/1999 | Babson et al. | |
| 5,885,530 | A | | 3/1999 | Babson et al. | |
| 6,410,252 | B1 | * | 6/2002 | Lehmann et al. | 435/7.94 |
| 6,410,334 | B1 | * | 6/2002 | Schmolz | 436/63 |

FOREIGN PATENT DOCUMENTS

WO   WO 00/08464   *   2/2000

OTHER PUBLICATIONS

Lolli et al, Aids Research and Human Retroviruses, 10, 115-120, 1994.*
The Merck Manual, Seventeenth Edition, Merck Research Laboratories, 1999. pp. 377-379, 1194-1195.*
Herbert et al, Dictionary of Immunology, Blackwell Scientific Publications, Third Edition, 1995, p. 172.*
Kabllan L. et al. (1990) Eur. J. Immunol., vol. 20, pp. 1085-1089, "Detection of Intracellular Expression and Secretion of Interferon-( at the Single-Cell Level after Activation of Human T cells with Tetanus Toxoid in vitro".
Benyoucef, S. et al., (1977) Pathologie Biologle, vol. 45(5), pp. 400-403. "An Interferon-( (IFN-() Based Whole Blood Assay to Detect T Cell Response to Antigens in HIV-1 Infected Patients".
Pais, T.F. et al. (1998) Immunology, vol. 95, pp. 69-75, "Analysis of T Cells Recruited During Delayed-Type Hypersensitivity to Purified Protein Derivative (PPD) Versus Challeng ewith Tuberculosis Infection".
Whist, S.K. et al. (2000) Veterinary Immunology and Immunopathology, vol. 73, pp. 207-218, "The Use of Interleukin-2-Receptor Expression as a Marker of Cell-Mediated Immunity in Goats Experimentally Infected with Mycobacterium avium ssp. Paratuberculosis".
Streeton, J.A., et al. (1998), International Journal of Tuberculosis and Lung Cancer, vol. 2(6), pp. 443-450, "Sensitivity and Specificity of a Gamma Interferon Blood Test for Tuberculosis Infection".
Baird, M. A., et al. (1995), Immunology and Cell Biology, vol. 73, pp. 537-543, "Dendrtitic Cell Presentation of PPD and 19kDa protein of Mycobacterium Tuberclusois and Energent T helper Cell Phenotype".
Brock, I. et al., (2001) International Journal of Tuberculosis and Lung Cancer, vol. 5(5), pp. 462-467, "Performance of Whole Blood IFN-(-test for Tuberculosis Diagnosis based on PPD or the Specific Antigens ESAT-6 and CFP-10".
De Groote, D. et al., (1996) Cancer Detection and Prevention, vol. 20(3), pp. 207-213, "Ex vivo Cytokine Production by Whole Blood Cells From Cancer Patients".
Shearer, G.M. and Clerici, M. (1994), Clinical Chemistry, vol. 40/11(B), pp. 2162-2165, "In vitro Analysis of Cell-Mediated Immunity Clinical Relevance".
Van Crevel, R. et al. (1999), Journal of Immunoglogical Methods, vol. 222, pp. 145-153, "Disease-Specific ex vivo Stimulation of Whole Blood for Cytokine Production: Applications in the Study of Tuberculosis".
Katial, R.K. et al. (2001), Clinical and Diagnostic Laboratory Immunology, vol. 8(2), pp. 339-345, "Cell-mediated Immune Response to Tuberculosis Antigens: Comparison of Skin Testing and Measurement of in vitro Gamma Interferon Production in Whole-Blood Culture".

(Continued)

*Primary Examiner*—David A Saunders
(74) *Attorney, Agent, or Firm*—Scully, Scott, Murphy & Presser, P.C.

(57) ABSTRACT

The present invention relates generally to a diagnostic assay and, more particularly, an assay for measuring cell-mediated immune reactivity. Even more particularly, the present invention provides an assay and a kit for measuring a cell-mediated response to an antigen using whole blood or other suitable biological sample. The assay may be conducted using ligands to immune effector molecules or at the nucleic acid level, screening for expression of genes encoding the immune effector molecules. The assay is useful in therapeutic and diagnostic protocols for human, livestock and veterinary and wild life applications.

64 Claims, 2 Drawing Sheets

OTHER PUBLICATIONS

Van Wauwe, J. et al., Infamm. Res. (1995), vol. 44, pp. 400-405, "Cytokine Production by Phytohemagglutinin-Stimulated Human Blood Cells: Effects of Corticosteroids, T Cell Immunosuppressants and Phosphodiesterase IV Inhibitors".

Devine, J.E., Therapeutic Drug Monitoring (1986), vol. 8, pp. 241-243, "Assessment of the Corvac Blood Collection Tube for Drub Specimen Processing".

Weber, B. et al., Journal of Virological Methods (1999), vol. 78, pp. 61-70, "Multicenter Evaluation of New Rapid Automated Human Immunodeficiency Virus Antigen Detection Assay".

McCurdy, H.H. et al., Journal of Forensic Sciences, vol. 34, No. 4, pp. 858-870 (1989), Studies on the Stability and Detection of Cocaine, Bezoylecgonine, and 11-nordelta-9-tetrahydrocannabinol-9-carboxylic Acid in Whole Blood Using Abusereen.

Lonlgro, J. et al., Laboratory Animal Science, vol. 35, No. 6, pp. 651-652 (1985), "Evaluation of Micro Serum Separation Tubes for Obtaining Serum Specimens Suitable for Serological Testing".

Bigos, et al., "Nine Color Eleven Parameter Immunophenotyping Using Three Laser Flow Cytometry", Cytometry, vol. 36, pp. 36-45 (1999).

Daneshvar, et al., "Detection of Biomolecules in the Near-infrared Spectral Region via a Fiber-optic Immunosensor", J. Immunol. Methods, vol. 226, pp. 119-128 (1999).

J.R. Durig, et al., "Fourier Transform Raman Spectroscopy of Brightly Colored Commercially Available Dyestuffs and Pigments", Journal of Raman Spectroscopy, vol. 24, pp. 281-285 (1993).

Eriksson, et al., "Lipid and Water Diffusion in Bicontinuous Cubic Phases Measured by NMR", Biophys, J., vol. 64, pp. 129-136 (1993).

Fu, et al., "A Microfabricated Fluorescence-activated Cell Sorter", Nature Biotechnology, vol. 17, pp. 1109-1111 (1999).

Lakowicz, et al., "Time-Resolved Fluorescence Spectroscopy and Imaging of DNA Labeled with DAPI and Hoechst 33342 Using Three-Photon Excitation", Biophysical Journal, vol. 72, pp. 567-578 (1997).

Lewis, et al., Erratum to "The Use of Fourier Transform Infrared (FT-IR) Spectroscopy to Study the State of Heterobifunctional Reactive Dyes", Dyes and Pigments, vol. 42, pp. 111-123 (1997).

Malemed, et al., Flow Cytometry and Sorting, 2nd Edition, New York, Wiley-Liss (1990).

Rahman, et al., "Infrared and Raman Spectra of A Single Resin Bead for Analysis of Solid-Phase Reactions and Use in Encoding Combinatorial Libraries", J. Org. Chem., vol. 63, pp. 6196-6199 (1998).

Rapaport, et al., "Visible Light Emission from Dyes Excited by Simultaneous Absorption of Two Different Frequency Beams of Light", Applied Physics Letters, vol. 74, No. 3, pp. 329-331 (1999).

Tawa, et al., "Poloarized Light-Induced Anisotropy in Polymer Films Doped with Az Dyes in the Photostationary State Studied by IR Spectroscopy", Mater. Res. Soc. Symp. Proc., vol. 488, pp. 885-890 (1998).

Youvan, et al., "Calibration of Fluorescence Resonance Energy Transfer in Microscopy Using Genetically Engineered GFP Derivatives on Nickel Chelating Beads", Biotechnology et alia, vol. 3, pp. 1-18 (1997).

"Iscove's Modified Dulbecco's Medium (IMDM) (1X) Liquid" [Online], Retrieved from the Internet: URL:http://www.invitrogen.com/content.cfm?pageId=95&fuseaction=MediaForm.dsp_mediaForm&productId=76> [retrieved on Nov. 6, 2006], XP002405686.

"RPMI Medium 1640 Powder" [Online] Retrieved from the Internet: URL:http://www.invitrogen.com/content.cfm?pageId=95 &fuseaction=MediaForm.dsp_mediaForm&productId=119> [retrieved on Nov. 6, 2006], XP002405687.

Gobin et al., Transfus, Clin. Biol. (2001), vol. 8, pp. 45-49, "Evaluation of Evacuated Blood Collection Tubes Analytical Performances for the Screening of Anti-HIV, anti-HTLV, anti-HCV, anti-HBc, anti-HBs, anti-CMV antibodies, and HBs, P24 HIV Antigens and for the Assay or Alanlne Aminotransferase".

Mole L., et al., Journal of Clinical Microbiology 1994, vol. 32, No., pp. 2212-2215, "Stabilities of Quantitative Plasma Culture for Human Immunodeficiency Virus, RNA, and p. 24 Antigen from Samples Collected in Vacutainer CPT and Standard Vacutainer Tubes".

* cited by examiner

DIAGNOSTIC ASSAY FOR MEASURING A CELL MEDIATED IMMUNE RESPONSE

BACKGROUND OF THE INVENTION

1. Field of the Invention

The present invention relates generally to a diagnostic assay and, more particularly, an assay for measuring cell-mediated immune reactivity. Even more particularly, the present invention provides an assay and a kit for measuring a cell-mediated response to an antigen using whole blood or other suitable biological sample. The assay may be conducted using ligands to immune effector molecules or at the nucleic acid level, screening for expression of genes encoding the immune effector molecules. The assay is useful in therapeutic and diagnostic protocols for human, livestock and veterinary and wild life applications.

2. Description of the Prior Art

Bibliographic details of references provided in the subject specification are listed at the end of the specification.

Reference to any prior art in this specification is not, and should not be taken as, an acknowledgment or any form of suggestion that this prior art forms part of the common general knowledge in any country.

Measurement of cell-mediated immune (CMI) responses is important for immune diagnosis of many infectious and autoimmune diseases, as a marker for immunocompetence, and for detection of T-cell responses to endogenous and exogenous antigens (i.e. vaccines).

Current methods for detecting CMI responses include skin tests measuring both immediate and delayed type hypersensitivity, lymphocyte proliferation assays and measurement of cytokines produced by purified mononuclear cells cultured with antigen.

Most in vitro methods for detecting CMI responses involve the purification of lymphocytes from whole blood, culturing these lymphocytes with an antigen for periods from 12 hours to 6 days and then detecting T-cell reactivity to the antigen. Older, established methods, such as the proliferation assay, use the uptake of radioactive isotopes by dividing T-cells as a marker for CMI reactivity. More recently, techniques such as a single cell assay (ELISpot) have been used to detect the number of T-cells producing certain cytokines in response to the antigenic stimulation.

Despite the existence of the previously used assays for measuring CMI responsiveness, the practical limitations of easily and accurately measuring CMI responses have hitherto precluded large scale adoption of these assays in standard and routine medical practice in the diagnosis of infectious disease, autoimmune disease and oncology.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention provides a method for measuring CMI in a subject by incubating a sample from the subject which comprises T-cells or other cells of the immune system with an antigen. Production of IFN-γ or other cytokine or immune effector molecule(s) is then detected. The presence or level of immune effector is then indicative of the level of cell mediated responsiveness of the subject.

Preferably, the sample is whole blood which is collected in a suitable container comprising the antigen. Optionally, a simple sugar such as dextrose is added to the incubation mixture.

Accordingly, one aspect of the present invention contemplates a method for measuring a CMI response in a subject, said method comprising collecting a sample from said subject wherein said sample comprises cells of the immune system which are capable of producing immune effector molecules following stimulation by an antigen, incubating said sample with an antigen and then measuring the presence of or elevation in the level of an immune effector molecule wherein the presence or level of said immune effector molecule is indicative of the capacity of said subject to mount a cell-mediated immune response.

Preferably, the subject is a human. The present invention contemplates, however, primates, livestock animals, laboratory test animals, companion animals and avian species as well as non-mammalian animals such as reptiles and amphibians. The assay has applications, therefore, in human, livestock, veterinary and wild life therapy and diagnosis.

In a preferred embodiment, the sample is whole blood which is collected in collection tubes containing the antigen or to which the antigen is added. Generally, blood is maintained in the presence of heparin. Heparin may be in the tube when blood is added or is added subsequently. The use of blood collection tubes is compatible with standard automated laboratory systems and these are amenable to analysis in large-scale and random access sampling. Blood collection tubes also minimize handling costs and reduces laboratory exposure to whole blood and plasma and, hence, reduces the risk of laboratory personnel from contracting a pathogenic agent such as human immunodeficiency virus HIV or hepatitis B virus (HBV). Furthermore, use of the collection tubes to conduct the incubation renders the assay far more sensitive than the previously used 24 well culture well plates.

The present invention provides an enhanced CMI assay, therefore, comprising use of a collection tube, optionally a simple sugar such as dextrose and the incubation step. The incubation step is preferably from 5 to 50 hours.

The immune effector molecule is preferably a cytokine such as but not limited to IFN-γ. The presence or level of immune effector may be determined at the level of the molecule itself or to the extent to which a gene is expressed.

The present invention further provides kits comprising reagents and compartments required to perform the assay. Generally, the kit further comprises a set of instructions.

The assay may also be automated or semi-automated and the automated aspects may be controlled by computer software.

The present invention still further contemplates a method of treatment of a pathological condition such as infection by a microorganism, parasite or virus, an autoimmune condition or cancer. The method comprises assessing the capacity of a subject to mount a cell-mediated immune response and then selecting a therapeutic protocol such as inducing CMI against a target antigen alone or in combination with other therapy.

A list of abbreviations used herein is provided in Table 1.

TABLE 1

Abbreviations

| ABBREVIATION | DESCRIPTION |
| --- | --- |
| CMI | cell-mediated immunity |
| CSF | colony stimulating factor |

TABLE 1-continued

Abbreviations

| ABBREVIATION | DESCRIPTION |
|---|---|
| ELISA | enzyme linked immunosorbent assay |
| ELISpot | single cell ELISA |
| G-CSF | granulocyte-CSF |
| GM-CSF | granulocyte, macrophage-CSF |
| HBV | hepatitis B virus |
| HIV | human immunodeficiency virus |
| IFN-γ | interferon-gamma |
| PPD | Mycobacterium-tuberculosis purified protein derivative |
| TNF-α | tumor necrosis factor |

DETAILED DESCRIPTION OF THE INVENTION

The present invention provides an assay of the potential or capacity of a subject to mount a CMI response. The assay is based on measuring immune effector molecule production by cells of the immune system in response to antigenic stimulation. The immune effectors may be detected using ligands such as antibodies specific for the effectors or by measuring the level of expression of genes encoding the effectors. The present invention provides, therefore, a means to determine the responsiveness of CMI in a subject and, in turn, provides a means for the diagnosis of infectious diseases, pathological conditions, level of immunocompetence and a marker of T-cell responsiveness to endogenous or exogenous antigens.

Accordingly, one aspect of the present invention contemplates a method for measuring a CMI response in a subject, said method comprising collecting a sample from said subject wherein said sample comprises cells of the immune system which are capable of producing immune effector molecules following stimulation by an antigen, incubating said sample with an antigen and then measuring the presence of or elevation in the level of an immune effector molecule wherein the presence or level of said immune effector molecule is indicative of the capacity of said subject to mount a cell-mediated immune response.

Reference to a "subject" includes a human or non-human species including primates, livestock animals (e.g. sheep, cows, pigs, horses, donkey, goats), laboratory test animals (e.g. mice, rats, rabbits, guinea pigs, hamsters), companion animals (e.g. dogs, cats), avian species (e.g. poultry birds, aviary birds), reptiles and amphibians. The present invention has applicability, therefore, in human medicine as well as having livestock and veterinary and wild life applications. Most preferably, however, the subject is a human and the CMI response assay has applications in screening for responsiveness to pathogenic microorganisms, viruses and parasites, potential for development or monitoring autoimmune conditions and for monitoring a subject's response to oncological challenge.

According to this preferred embodiment, therefore, the present invention provides a method for measuring a CMI response in a human subject, said method comprising collecting a sample from said human subject wherein said sample comprises cells of the immune system which are capable of producing immune effector molecules following stimulation by an antigen, incubating said sample with an antigen and then measuring the presence of or elevation in the level of an immune effector molecule wherein the presence or level of said immune effector molecule is indicative of the capacity of said human subject to mount a cell-mediated immune response.

Reference to "immune cells" includes cells such as lymphocytes including natural killer (NK) cells, T-cells, (CD4$^+$ and/or CD8$^+$ cells), B-cells, macrophages and monocytes, dendritic cells or any other cell which is capable of producing an effector molecule in response to direct or indirect antigen stimulation. Conveniently, the immune cells are lymphocytes and more particularly T-lymphocytes.

The immune effector molecules may be any of a range of molecules which are produced in response to cell activation or stimulation by an antigen. Although an interferon (IFN) such as IFN-γ is a particularly useful immune effector molecule, others include a range of cytokines such as interleukins (IL), e.g. IL-2, IL-4, IL-10 or IL-12, tumor necrosis factor alpha (TNF-α), a colony stimulating factor (CSF) such as granulocyte (G)-CSF or granulocyte macrophage (GM)-CSF amongst many others such as complement or components in the complement pathway.

Accordingly, in another preferred embodiment, the present invention provides a method for measuring a CMI response in a subject, said method comprising collecting a sample from said subject wherein said sample comprises cells of the immune system which are capable of producing IFN-γ molecules following stimulation by an antigen, incubating said sample with an antigen and then measuring the presence of or elevation in the level of an IFN-γ molecule wherein the presence or level of said IFN-γ molecule is indicative of the capacity of said subject to mount a cell-mediated immune response.

As far as the preferred embodiment extends to humans is concerned, the present invention further provides a method for measuring a CMI response in a human subject, said method comprising collecting a sample from said subject wherein said sample comprises cells of the immune system which are capable of producing IFN-γ molecules following stimulation by an antigen, incubating said sample with an antigen and then measuring the presence or elevation in level of an IFN-γ molecule wherein the presence or level of said IFN-γ molecule is indicative of the capacity of said human subject to mount a cell-mediated immune response.

The sample collected from the subject is generally deposited into a blood collection tube. A blood collection tube includes a blood draw tube or other similar vessel. Conveniently, when the sample is whole blood, the blood collection tube is heparinized. Alternatively, heparin is added to the tube after the blood is collected. Notwithstanding that whole blood is the preferred and most convenient sample, the present invention extends to other samples containing immune cells such as lymph fluid, cerebral fluid, tissue fluid and respiratory fluid including nasal and pulmonary fluid.

The use of blood collection tubes is compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as HIV or hepatitis B virus (HBV).

Combining the incubation step with the collection tube is particularly efficacious and enhances the sensitivity of the assay as does the optional feature of incubating the cells in the presence of a sample sugar such as dextrose.

The cells of the CMI system lose the capacity to mount a CMI response in whole blood after extended periods following blood draw from the subject, and responses without intervention are often severely reduced or absent 24 hours following blood draw. The reduction of labor and need for specialized plasticware allows CMI stimulation with antigens to be performed at the point of care locations such as physicians' offices, clinics, outpatient facilities and veterinary clinics or on farms. Once antigen stimulation is complete, the requirement for fresh and active cells no longer exists. IFN-γ and other cytokines or immune effector molecules are stable in plasma and, thus, the sample can be stored, or shipped without special conditions or rapid time requirements in a similar fashion to standard serum samples used for other infectious disease or other disease diagnosis.

The incubation step may be from 5 to 50 hours, more preferably 5 to 40 hours and even more preferably 8 to 24 hours or a time period in between.

Accordingly, another preferred embodiment of the present invention contemplates a method for measuring a CMI response in a subject including a human subject, said method comprising collecting a sample of whole blood from said subject, incubating said whole blood sample with an antigen and then measuring the presence or elevation in level of an immune effector molecule such as IFN-γ wherein the presence or level of said immune effector molecule is indicative of the capacity of said subject to mount a cell-mediated immune response.

In one preferred embodiment, the incubation step is conducted in the presence of a simple sugar such as dextrose.

The ability to measure CMI is important for assessing a subject's ability to respond to an infection by an pathogenic agent such as a microorganism or virus or parasite, to mount an autoimmune response such as in diabetes or to protect against cancers or other oncological conditions. Consequently, reference to "measuring a CMI response in a subject" includes an encompasses immune diagnosis of infectious and autoimmune diseases, a marker for immunocompetence and the detection of T-cell responses to endogenous and/or exogenous antigens (including a measure of the efficacy of a vaccine) as well as a marker for inflammatory diseases and cancer.

Autoimmune diseases contemplated herein include inter alia Alopecia Areata, Ankylosing Spondylitis, Antiphospholipid Syndrome, Autoimmune Addison's Disease Multiple Sclerosis, Autoimmune disease of the adrenal gland, Autoimmune Hemolytic Anemia, Autoimmune Hepatitis, Autoimmune oophoritis and orchitis, Behcet's Disease, Bullous Pemphigoid, Cardiomyopathy, Celiac Sprue-Dermatitis, Chronic Fatigue Syndrome (CFIDS), Chronic Inflam. Demyelinating, Chronic Inflam. Polyneuropathy, Churg-Strauss Syndrome, Cicatricial Pemphigoid, CREST Syndrome, Cold Agglutinin Disease, Crohn's Disease, Dermatitis herpetiformis, Discoid Lupus, Essential Mixed Cryoglobulinemia, Fibromyalgia, Glomerulonephritis, Grave's Disease, Guillain-Barre, Hashimoto's Thyroiditis, Idiopathic Pulmonary Fibrosis, Idiopathic Thrombocytopenia Purpura (ITP), IgA Nephropathy Insulin Dependent Diabetes (Type I), Lichen Planus, Lupus, Meniere's Disease, Mixed Connective Tissue Disease, Multiple sclerosis, Myasthenia Gravis, Myocarditis, Pemphigus Vulgaris, Pernicious Anemia, Polyarteritis Nodosa, Polychondritis, Polyglancular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiff-Man Syndrome, Systemic lupus erythematosus, Takayasu Arteritis, Temporal Arteritis/Giant Cell Arteritis, Ulcerative Colitis, Uveitis, Vasculitis and Vitiligo.

It is generally important to assess the potential or actual CMI responsiveness in these individuals.

Other disease conditions contemplated include inflammatory disease conditions.

Examples of inflammatory disease conditions contemplated by the present invention include but are not limited to those disease and disorders which result in a response of redness, swelling, pain, and a feeling of heat in certain areas that is meant to protect tissues affected by injury or disease. Inflammatory diseases which can be treated using the methods of the present invention, include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, Chronic Inflammatory Demyelinating Polyneuropathy, Chronic Inflammatory Demyelinating Polyradiculoneuropathy, Chronic Inflammatory Demyelinating Polyneuropathy, Chronic Inflammatory Demyelinating Polyradiculoneuropathy.

Cancer therapy also is somewhat dependent on CMI. Cancers contemplated herein include: a group of diseases and disorders that are characterized by uncontrolled cellular growth (e.g. formation of tumor) without any differentiation of those cells into specialized and different cells. Such diseases and disorders include ABL1 protooncogene, AIDS Related Cancers, Acoustic Neuroma, Acute Lymphocytic Leukaemia, Acute Myeloid Leukaemia, Adenocystic carcinoma, Adrenocortical Cancer, Agnogenic myeloid metaplasia, Alopecia, Alveolar soft-part sarcoma, Anal cancer, Angiosarcoma, Aplastic Anaemia, Astrocytoma, Ataxia-telangiectasia, Basal Cell Carcinoma (Skin), Bladder Cancer, Bone Cancers, Bowel cancer, Brain Stem Glioma, Brain and CNS Tumours, Breast Cancer, CNS tumours, Carcinoid Tumours, Cervical Cancer, Childhood Brain Tumours, Childhood Cancer, Childhood Leukaemia, Childhood Soft Tissue Sarcoma, Chondrosarcoma, Choriocarcinoma, Chronic Lymphocytic Leukaemia, Chronic Myeloid Leukaemia, Colorectal Cancers, Cutaneous T-Cell Lymphoma, Dermatofibrosarcoma-protuberans, Desmoplastic-Small-Round-Cell-Tumour, Ductal Carcinoma, Endocrine Cancers, Endometrial Cancer, Ependymoma, Esophageal Cancer, Ewing's Sarcoma, Extra-Hepatic Bile Duct Cancer, Eye Cancer, Eye: Melanoma, Retinoblastoma, Fallopian Tube cancer, Fanconi Anaemia, Fibrosarcoma, Gall Bladder Cancer, Gastric Cancer, Gastrointestinal Cancers, Gastrointestinal-Carcinoid-Tumour, Genitourinary Cancers, Germ Cell Tumours, Gestational-Trophoblastic-Disease, Glioma, Gynaecological Cancers, Haematological Malignancies, Hairy Cell Leukaemia, Head and Neck Cancer, Hepatocellular Cancer, Hereditary Breast Cancer, Histiocytosis, Hodgkin's Disease, Human Papillomavirus, Hydatidiform mole, Hypercalcemia, Hypopharynx Cancer, IntraOcular Melanoma, Islet cell cancer, Kaposi's sarcoma, Kidney Cancer, Langerhan's-Cell-Histiocytosis, Laryngeal Cancer, Leiomyosarcoma, Leukaemia, Li-Fraumeni Syndrome, Lip Cancer, Liposarcoma, Liver Cancer, Lung Cancer, Lymphedema, Lymphoma, Hodgkin's Lymphoma, Non-Hodgkin's Lymphoma, Male Breast Cancer, Malignant-Rhabdoid-Tumour-of-Kidney, Medulloblastoma, Melanoma, Merkel Cell Cancer, Mesothelioma, Metastatic Cancer, Mouth Cancer, Multiple Endocrine Neoplasia, Mycosis Fungoides, Myelodysplastic Syndromes, Myeloma, Myeloproliferative Disorders, Nasal Cancer, Nasopharyngeal Cancer, Nephroblastoma, Neuroblastoma, Neurofibromatosis, Nijmegen Breakage Syndrome, Non-Melanoma Skin Cancer, Non-Small-Cell-Lung-Cancer-(NSCLC), Ocular Cancers, Oesophageal Cancer, Oral cavity Cancer, Oropharynx Cancer, Osteosarcoma, Ostomy Ovarian Cancer, Pancreas Cancer, Paranasal Cancer, Parathyroid Cancer, Parotid Gland Cancer, Penile Cancer, Peripheral-Neuroectodermal-Tumours, Pituitary Cancer, Polycythemia vera, Prostate Cancer, Rare-cancers-and-associated-disorders, Renal Cell Carcinoma, Retinoblastoma, Rhabdomyosarcoma, Rothmund-Thomson Syndrome, Salivary Gland Cancer, Sarcoma, Schwannoma, Sezary syndrome, Skin Cancer, Small Cell Lung Cancer (SCLC), Small Intestine Cancer, Soft Tissue Sarcoma, Spinal Cord Tumours, Squamous-Cell-Carcinoma-(skin), Stomach Cancer, Synovial sarcoma, Testicular Cancer, Thymus Cancer, Thyroid Cancer, Transitional-Cell-Cancer-(bladder), Transitional-Cell-Cancer-(renal-pelvis-/-ureter), Trophoblastic Cancer, Urethral Cancer, Urinary System Cancer, Uroplakins, Uterine sarcoma, Uterus Cancer, Vaginal Cancer, Vulva Cancer, Waldenstrom's-Macroglobulinemia, Wilms' Tumour.

Any of a range of antigens may be tested such as those specific for a particular organism, virus, autoantigen or cancer cell. Alternatively, more general agents may be used to test generic capacity of a cell-mediated immune response. Examples of the latter include PPD from *M. tuberculosis* and tetanus toxoid. In general, however, any peptide, polypeptide or protein, carbohydrate, glycoprotein, phospholipid, phosphoprotein or phospholipoprotein or non-protein chemical agent may be used in the assay system.

As stated above, detection of the immune effector molecules may be made at the protein or nucleic acid levels. Consequently, reference to "presence or level of said immune effector molecule" includes direct and indirect data. For example, high levels of IFN-γ mRNA is indirect data showing increased levels of IFN-γ.

Ligands to the immune effectors are particularly useful in detecting and/or quantitating these molecules. Antibodies to the immune effectors are particularly useful. Techniques for the assays contemplated herein are known in the art and include, for example, sandwich assays, ELISA and ELISpot. Reference to "antibodies" includes parts of antibodies, mammalianized (e.g. humanized) antibodies, recombinant or synthetic antibodies and hybrid and single chain antibodies.

Both polyclonal and monoclonal antibodies are obtainable by immunization with the immune effectors or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting an immune effector in a sample comprising immune cells from a subject, said method comprising contacting said sample or an aliquot of said sample with an antibody specific for said immune effector or antigenic fragment thereof for a time and under conditions sufficient for an antibody-effector complex to form, and then detecting said complex.

A sample includes whole blood. This method includes micro-arrays and macro-arrays on planar or spherical solid supports. A micro- or macro-array is useful.

A wide range of immunoassay techniques are available as can be seen by reference to U.S. Pat. Nos. 4,016,043, 4,424,279 and 4,018,653.

The following is a description of one type of assay. An unlabeled antibody is immobilized on a solid substrate and the sample to be tested for the immune effectors (e.g. antigens) brought into contact with the bound molecule. After a suitable period of incubation, for a period of time sufficient to allow formation of an antibody-antigen complex, a second antibody specific to the antigen, labeled with a reporter molecule capable of producing a detectable signal, is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of antigen. This generalized technique is well known to those skilled in the art as would be any of a number of variations.

In these assays, a first antibody having specificity for the instant immune effectors is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, spheres, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the hapten.

There are many variations to this assay. One particularly useful variation is a simultaneous assay where all or many of the components are admixed substantially simultaneously.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. Examples of suitable fluorophores are provided in Table 2. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Again, the present invention extends to a substantially simultaneous assay.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest. Immunofluorescene and EIA techniques are both very well established in the art and are particularly preferred for the present method. However, other reporter molecules, such as radioisotope, chemiluminescent or bioluminescent molecules, may also be employed.

There are a range of other detection systems which may be employed including colloidal gold and all such detection systems are encompassed by the present invention.

The present invention also contemplates genetic assays such as involving PCR analysis to detect RNA expression products of a genetic sequence encoding an immune effector.

In one embodiment, PCR is conducted using pairs of primers, one or both of which are generally labeled with the same or a different reporter molecule capable of giving a distinguishable signal. The use of fluorophores is particularly useful in the practice of the present invention. Examples of suitable fluorophores may be selected from the list given in Table 2. Other labels include luminescence and phosphorescence as well as infrared dyes. These dyes or fluorophores may also be used as reporter molecules for antibodies.

TABLE 2

| Probe | Ex$^1$ (nm) | Em$^2$ (nm) |
|---|---|---|
| List of suitable fluorophores | | |
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3, 5 | 581 | 596; (640) |
| Cy5 | (625); 650 | 670 |
| Cy5, 5 | 675 | 694 |
| Cy7 | 743 | 767 |
| Nucleic acid probes | | |
| Hoeschst 33342 | 343 | 483 |
| DAPI | 345 | 455 |
| Hoeschst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bomnide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |
| Propidium Iodide (PI) | 536 | 617 |
| TOTO-3, TO-PRO-3 | 642 | 661 |
| LDS 751 | 543; 590 | 712; 607 |
| Fluorescent Proteins | | |
| Y66F | 360 | 508 |
| Y66H | 360 | 442 |
| EBFP | 380 | 440 |
| Wild-type | 396, 475 | 50, 503 |
| GFPuv | 385 | 508 |
| ECFP | 434 | 477 |
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |

TABLE 2-continued

List of suitable fluorophores

| Probe | Ex[1] (nm) | Em[2] (nm) |
|---|---|---|
| Other probes | | |
| Monochlorobimane | 380 | 461 |
| Calcein | 496 | 517 |

[1]Ex: Peak excitation wavelength (nm)
[2]Em: Peak emission wavelength (nm)

Any suitable method of analyzing fluorescence emission is encompassed by the present invention. In this regard, the invention contemplates techniques including but not restricted to 2-photon and 3-photon time resolved fluorescence spectroscopy as, for example, disclosed by Lakowicz et al., *Biophys. J.* 72: 567, 1997, fluorescence lifetime imaging as, for example, disclosed by Eriksson et al., *Biophys. J.* 2: 64, 1993 and fluorescence resonance energy transfer as, for example, disclosed by Youvan et al., *Biotechnology* et elia 3: 1-18, 1997.

Luminescence and phosphorescence may result respectively from a suitable luminescent or phosphorescent label as is known in the art. Any optical means of identifying such label may be used in this regard.

Infrared radiation may result from a suitable infrared dye. Exemplary infrared dyes that may be employed in the invention include but are not limited to those disclosed in Lewis et al., *Dyes Pigm.* 42(2): 197, 1999, Tawa et al., *Mater. Res. Soc. Symp. Proc.* 488 [Electrical, Optical and Magnetic Properties of Organic Solid-State Materials IV], 885-890, Daneshvar et al., *J. Immunol. Methods* 226(1-2): 119-128, 1999, Rapaport et al., *Appl. Phys. Lett.* 74(3): 329-331, 1999 and Durig et al., *J. Raman Spectrosc.* 24(5): 281-285, 1993. Any suitable infrared spectroscopic method may be employed to interrogate the infrared dye. For instance, fourier transform infrared spectroscopy as, for example, described by Rahman et al., *J. Org. Chem.* 63: 6196, 1998 may be used in this regard.

Suitably, electromagnetic scattering may result from diffraction, reflection, polarization or refraction of the incident electromagnetic radiation including light and X-rays. Such scattering can be used to quantitate the level of mRNA or level of protein.

Flow cytometry is particularly useful in analyzing fluorophore emission.

As is known in the art, flow cytometry is a high throughput technique which involves rapidly analyzing the physical and chemical characteristics of particles (e.g. labeled mRNA, DNA or proteins) as they pass through the path of one or more laser beams while suspended in a fluid stream. As each particle intercepts the laser beam, the scattered light and fluorescent light emitted by each cell or particle is detected and recorded using any suitable tracking algorithm as, for example, described hereunder.

A modern flow cytometer is able to perform these tasks up to 100,000 cells/particles $s^{-1}$. Through the use of an optical array of filters and dichroic mirrors, different wavelengths of fluorescent light can be separated and simultaneously detected. In addition, a number of lasers with different excitation wavelengths may be used. Hence, a variety of fluorophores can be used to target and examine, for example, different immune effectors within a sample or immune effectors from multiple subjects.

Suitable flow cytometers which may be used in the methods of the present invention include those which measure five to nine optical parameters (see Table 3) using a single excitation laser, commonly an argon ion air-cooled laser operating at 15 mW on its 488 nm spectral line. More advanced flow cytometers are capable of using multiple excitation lasers such as a HeNe laser (633 nm) or a HeCd laser (325 nm) in addition to the argon ion laser (488 or 514 nm).

TABLE 3

Exemplary optical parameters which may be measured by a flow cytometer.

| Parameter | Acronym | Detection angle form incident laser beam | Wavelength (nm) |
|---|---|---|---|
| Forward scattered light | FS | 2-5° | 488* |
| Side scattered light | SS | 90° | 488* |
| "Green" fluorescence | FL1 | 90° | 510-540[†] |
| "Yellow" fluorescence | FL2 | 90° | 560-580[†] |
| "Red" fluorescence | FL3 | 90° | >650[#] |

*using a 488 nm excitation laser
[†]width of bandpass filter
[#]longpass filter

For example, Biggs et al., *Cytometry* 36: 36-45, 1999 have constructed an 11-parameter flow cytometer using three excitation lasers and have demonstrated the use of nine distinguishable fluorophores in addition to forward and side scatter measurements for purposes of immunophenotyping (i.e. classifying) particles. The maximum number of parameters commercially available currently is 17: forward scatter, side scatter and three excitation lasers each with five fluorescence detectors. Whether all of the parameters can be adequately used depends heavily on the extinction coefficients, quantum yields and amount of spectral overlap between all fluorophores (Malemed et al., "Flow cytometry and sorting", $2^{nd}$ Ed., New York, Wiley-Liss, 1990). However, it will be understood that the present invention is not restricted to any particular flow cytometer or any particular set of parameters. In this regard, the invention also contemplates use in place of a conventional flow cytometer, a microfabricated flow cytometer as, for example, disclosed by Fu et al., *Nature Biotechnology* 17: 1109-1111, 1999.

The assay of the present invention may be automated or semi-automated for high throughput screening or for screening for a number of immune effectors from the one subject. The automation is conveniently controlled by computer software.

The present invention contemplates a computer program product, therefore, for assessing the presence or absence or the level of one or more immune effectors, said product comprising:

(1) code that receives, as input values, the identity of a reporter molecule associated with a labeled mRNA or antibody:

(2) code that compares said input values with reference values to determine the level of reporter molecules and/or the identity of the molecule to which the reporter molecule is attached; and (3) a computer readable medium that stores the codes.

Still another aspect of the present invention extends to a computer for assessing the presence or absence or level of one or more immune effectors, said computer comprises:

(1) a machine-readable data storage medium comprising a data storage material encoded with machine-readable data, wherein said machine-readable data comprise input values which identify a reporter molecule associated with a labeled mRNA or antibody;

(2) a working memory for storing instructions for processing said machine-readable data;

(3) a central-processing unit coupled to said working memory and to said machine-readable data storage medium, for processing said machine readable data to compare said values to provide an assessment of the identity or level of reporter molecules or of molecules to which they are attached; and (4) an output hardware coupled to said central processing unit, for receiving the results of the comparison.

Figure 1:
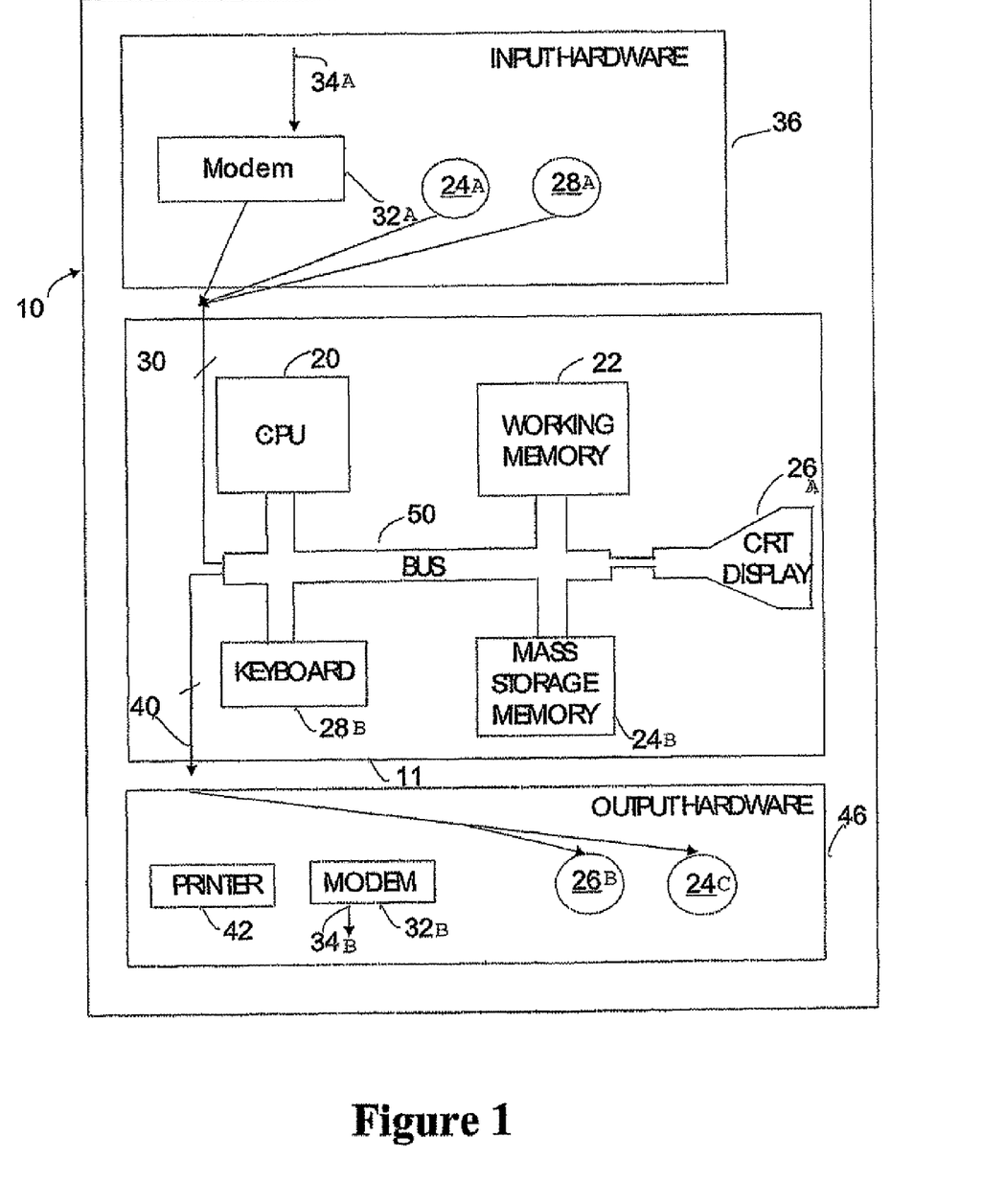
FIG. 1 is a diagrammatic representation of a system used to carry out the instructions encoded by the storage medium.

A version of these embodiments is presented in FIG. 1, which shows a system 10 including a computer 11 comprising a central processing unit ("CPU") 20, a working memory 22 which may be, e.g. RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD. Alternatively, ROM drives or disk drives 24 in conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a synthetic polynucleotide sequence or a synthetic polypeptide sequence as described herein. Output hardware might also include a printer 42, so that hard copy output may be produced, or a disk drive 24, to store system output for later use.

In operation, CPU 20 coordinates the use of the various input and output devices 36,46 coordinates data accesses from mass storage 24 and accesses to and from working memory 22, and determines the sequence of data processing steps. A number of programs may be used to process the machine readable data of this invention. Exemplary programs may use, for example, the following steps:

(1) inputting input values which identifies a reporter molecule associated with a labeled mRNA or antibody;

(2) assessing including comparing said input values with reference values to determine the level of reporter molecule and/or the identity of the molecule to which the reporter molecule is attached; and (3) outputting the results of the assessment.

Figure 2:
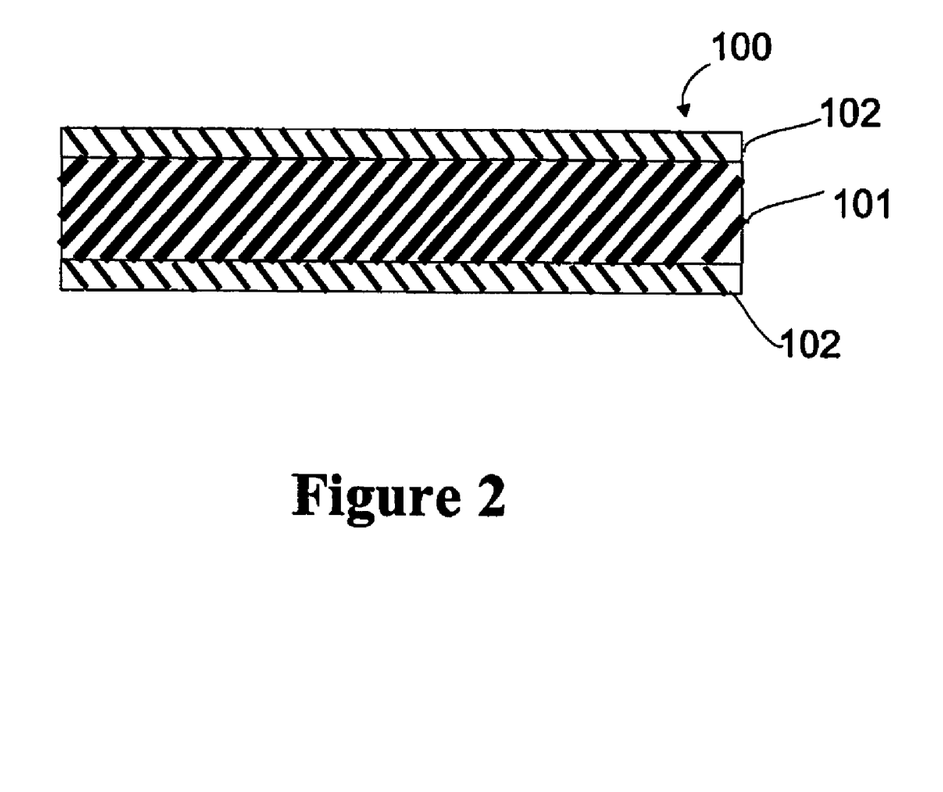
FIG. 2 is a diagrammatic representation of a cross-section of a magnetic storage medium.

FIG. 2 shows a cross section of a magnetic data storage medium 100 which can be encoded with machine readable data, or set of instructions, for assessing the level of an immune effector which can be carried out by a system such as system 10 of FIG. 1. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening for receiving the spindle of a disk drive or other data storage device 24. The magnetic domains of coating 102 of medium 100 are polarized or oriented so as to encode in manner which may be conventional, machine readable data for execution by a system such as system 10 of FIG. 1.

Figure 3:
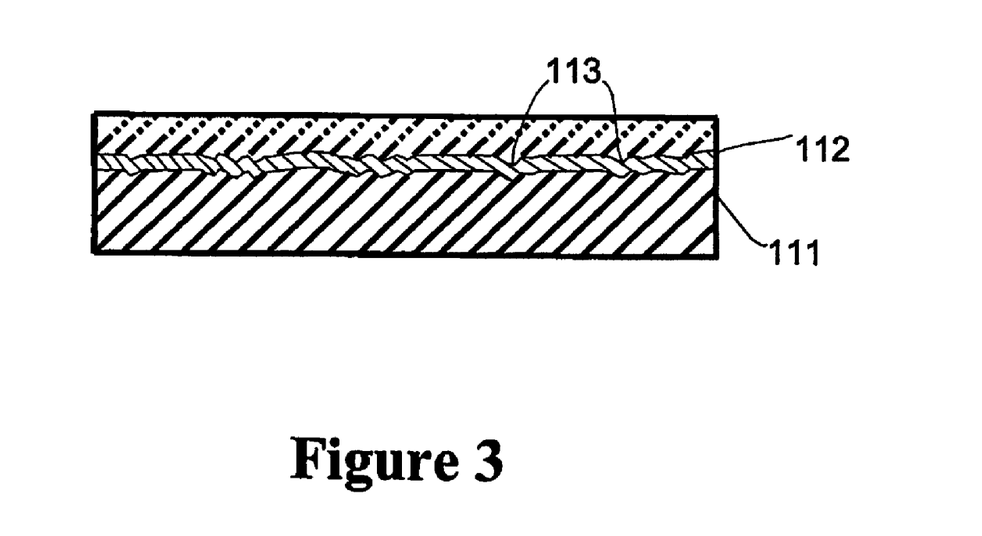
FIG. 3 is a diagrammatic representation of a cross-section of an optically readable data storage system.

FIG. 3 shows a cross section of an optically readable data storage medium 110 which also can be encoded with such a machine-readable data, or set of instructions, for designing a synthetic molecule of the invention, which can be carried out by a system such as system 10 of FIG. 1. Medium 110 can be a conventional compact disk read only memory (CD-ROM) or a rewritable medium such as a magneto-optical disk, which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

The present invention further contemplates a kit for assessing a subject's capacity to mount a cell mediated response. The kit is conveniently in compartmental form with one or more compartments adapted to receive a sample from a subject such as whole blood. That compartment or another compartment may also be adapted to contain heparin where the sample is whole blood with or without a simple sugar such as dextrose. The simple sugar may also be maintained in a separate container.

Generally, the kit is in a form which is packaged for sale with a set of instructions. The instructions would generally be in the form of a method for measuring a CMI response in a subject, said method comprising collecting a sample from said subject wherein said sample comprises cells of the immune system which are capable of producing immune effector molecules following stimulation by an antigen, incubating said sample with an antigen and then measuring the presence or elevation in level of an immune effector molecule wherein the presence or level of said immune effector molecule is indicative of the capacity of said subject to mount a cell-mediated immune response.

The present invention further provides a method of treatment of a subject having a pathogenic infection, an autoimmune disorder or cancer or a propensity for developing such a disorder, said method comprising assessing the ability for said subject to mount a cell mediated immune response by the method of measuring a CMI response in a subject, said method comprising collecting a sample from said subject wherein said sample comprises cells of the immune system which are capable of producing immune effector molecules following stimulation by an antigen, incubating said sample with an antigen and then measuring the presence of or elevation in the level of an immune effector molecule wherein the presence or level of said immune effector molecule is indicative of the capacity of said subject to mount a cell-mediated immune response and then selecting a suitable therapeutic protocol.

The present invention is further described by the following non-limiting Examples.

EXAMPLE 1

Development of Assay

Heparinized blood samples were collected from consenting volunteers or donors. Blood samples were collected into Vacuette [registered trade mark] tubes (Greiner Bio-one, Germany).

Aliquots of the blood samples were incubated with either *Mycobacterium tuberculosis* purified protein derivative (PPD, Cellestis Limited, Australia), Tetanus toxoid (CSL Limited, Australia), phytohemagglutinin (Cellestis Limited, Australia) or saline control in a number of different sized blood collection tubes as well as the standard 24-well tissue culture plates recommended by the manufacturers of the bovine whole blood IFN-γ test (Bovigam [registered trade mark], CSL Ltd.) or the human Quantiferon [registered trade mark] test (Cellestis Limited, Australia).

In some experiments, dextrose was added at various concentrations to the blood before initiation of incubation.

Antigen stimulated blood samples were incubated for 16 to 24 hours at 37° C., after which plasma was harvested from above the settled blood cells. The amount of IFN-γ present in each plasma sample was then quantified using the Quantiferon-TB [registered trade] ELISA (Cellestis Limited, Australia) as per the manufacturer's instructions. Samples stimulated with the tetanus toxoid antigen and the saline control were also tested using a more sensitive ELISA for IFN-γ (Quantiferon-CMI; Cellestis Limited, Australia) as per the manufacturer's instructions.

ELISA optical density values for IFN-γ standards run on each ELISA plate were used to construct a standard curve from which the amount of IFN-γ present in each of the test plasma samples was converted to IU/mL values.

EXAMPLE 2

Evaluating the Effect of Adding Dextrose to Blood before Culture with Antigen

Two blood samples were collected from volunteers and 8×1 mL aliquots added to individual wells of a 24-well tissue culture plate. The four antigens provided with the Quantiferon-TB test, Saline control (Nil), *M. tuberculosis* PPD (Hu PPD), *M. avium* PPD (Av PPD) and phytohemagglutinin (Mitogen), were added to duplicate wells containing blood. To one set of the duplicate wells, dextrose was added to a final concentration of 2 mg/mL. The plates were shaken for 1 minute before incubation at 37° C. for 20 hours in a humidified atmosphere. Plasma samples were collected and the concentrations of IFN-γ were quantified using the Quantiferon-TB [registered trade] ELISA.

The data demonstrate that the addition of dextrose to the blood, prior to incubation with antigen, resulted in an increase (1.4 to 2.2 fold) in the production of IFN-γ when stimulated with either of the PPD antigens (Table 4). In contrast, there was no increase in IFN-γ detected with the addition of dextrose to blood stimulated with the saline negative control. For blood samples stimulated with Mitogen, there was a slight increase in IFN-γ detected for one of the donors and a slight decrease for the other.

TABLE 4

Concentration of IFN-γ in IU/mL found for each plasma sample. Blood had been stimulated with antigen either with or without dextrose at a concentration of 2 mg/mL.

| | | Stimulation antigen | | |
|---|---|---|---|---|
| | | HuPPD | AvPPD | Mitogen |
| Donor 1 | −Dextrose | 96.20 | 54.68 | 28.67 |
| | +Dextrose | 142.25 | 76.50 | 25.71 |
| | Fold increase with dextrose | 1.48 | 1.40 | 0.90 |
| Donor 2 | −Dextrose | 71.34 | 31.55 | 108.72 |
| | +Dextrose | 134.47 | 67.62 | 122.76 |
| | Fold increase with dextrose | 1.88 | 2.14 | 1.13 |

EXAMPLE 3

Determining the Effect of Incubating Blood with Antigen in a Blood Collection Tube Versus a 24-well Tissue Culture Plate Heparinized blood from 15 Blood Bank donors was dispensed (1 mL aliquots) into both 24-well plates and Vacuette [registered trade mark] tubes containing 125 µL of HuPPD solution as supplied with the Quantiferon-TB [registered trade] kit. The 24-well plates were shaken for 1 minute and the capped Vacuette [registered trade mark] tubes mixed for 20 seconds by vortexing before incubation at 37° C. for 20 hours in a humidified atmosphere. The next day, plasma samples were collected from each incubation well and tube and the relative amounts of IFN-γ estimated using the Quantiferon-TB [registered trade] ELISA.

Table 5 shows that for all blood samples there was an increase in the amount of IFN-γ detected for the samples that had been incubated in the blood collection tubes. This increase ranged from 1.1 times to 16.3 times the amount of IFN-γ produced in the 24-well plate, with a mean increase of 4.7 times. Blood samples demonstrating smaller increases in IFN-γ production were generally those demonstrating very low levels of response to the HuPPD.

TABLE 5

Amount of IFN-γ detected from 1 mL blood samples incubated with HuPPD in either a 24-well tissue culture plate or a 2 mL blood collection tube

| Donor | HuPPD 24-well (control) | HuPPD Blood collection tube | Fold increase (Tube/24-well) |
|---|---|---|---|
| 1 | 0.025* | 0.044 | 1.8 |
| 2 | 0.056 | 0.765 | 13.7 |
| 3 | 0.230 | 0.852 | 3.7 |
| 4 | 0.069 | 0.428 | 6.2 |
| 5 | 0.034 | 0.058 | 1.7 |
| 6 | 0.084 | 0.135 | 1.6 |
| 7 | 1.196 | 0.725 | 3.7 |
| 8 | 0.030 | 0.215 | 7.2 |
| 9 | 0.087 | 1.422 | 16.3 |
| 10 | 0.032 | 0.057 | 1.8 |
| 11 | 0.029 | 0.032 | 1.1 |
| 12 | 0.037 | 0.138 | 3.7 |
| 13 | 0.036 | 0.057 | 1.6 |
| 14 | 0.067 | 0.121 | 1.8 |
| 15 | 0.292 | 0.213 | 4.2 |
| | Mean fold increase | | 4.7 |

*Optical density @ 450/620 nm

EXAMPLE 4

Effect of Incubation of Blood with Antigens in Blood Collection Tubes-2

Twenty heparinized blood samples were collected from blood bank donors and 3×1 mL aliquots were dispensed into individual wells of a 24-well tissue culture tray. To the respective wells, 125 µL of Saline, HuPPD or Mitogen were added. After shaking, the culture trays were incubated for 20 hours at 37° C. in a humidified atmosphere, before harvesting of plasma samples.

One mL aliquots of blood were also added to duplicate Vacuette [registered trade mark] tubes (Greiner Bio-one, Germany), which had previously had the same antigens as above added. The capped tubes were then mixed for 20 seconds using a vortex mixer and incubated for 20 hours at 37° C., before harvesting of plasma samples.

All plasma samples were tested for IFN-γ content using the standard Quantiferon-TB [registered trade mark] ELISA system. Threshold of detection was 2 IU/mL in this ELISA system.

The data in Table 6 show that for blood samples stimulated with human PPD, there was an increase in IFN-γ detected when the blood incubations had been performed in a blood collection tube rather than the 24-well tissue culture plate. For 5 of the 20 donor blood samples there was negligible response to the PPD antigen in either tissue culture plate or blood collection tube. For the remaining 15 blood samples, 12 demonstrated an increase in IFN-γ production with the in-tube incubation, one did not alter, and two showed a decrease.

In contrast to the results for the protein antigen HuPPD, incubation of blood in the blood collection tubes in the presence of the mitogen phytohemagglutinin generally resulted in lower levels of IFN-γ production than seen for the same samples incubated in 24-well plates. Such a difference may be expected due to the different mechanism of T-cell stimulation induced by the directly acting mitogen as compared to the immune mechanism stimulated by antigen/antigen presenting cell/T-cell interaction.

TABLE 6

Amount of IFN-γ detected from 1 mL blood samples incubated with HuPPD or mitogen in either a 24-well tissue culture plate or a blood collection tubes

| Donor | Human PPD 24-well | Human PPD Tube | Tube/24-well | Mitogen 24-well | Mitogen Tube | Tube/24-well |
|---|---|---|---|---|---|---|
| 1 | *3.32 | 1.79+ | NA | 7.69 | 3.52 | 0.46 |
| 2 | 52.52 | 93.05 | 1.77 | 83.34 | 61.94 | 0.74 |
| 3 | 20.46 | 51.87 | 2.54 | 1.13 | 13.13 | NA |
| 4 | 2.02 | 7.72 | 3.82 | 10.04 | 7.95 | 0.79 |
| 5 | 71.19 | 120.82 | 1.70 | 6.85 | 3.45 | 0.05 |
| 6 | 3.55 | 4.11 | 1.16 | 12.32 | 13.32 | 1.08 |
| 7 | 0.00 | 0.09 | NA | 8.77 | 5.29 | 0.60 |
| 8 | 3.05 | 4.61 | 1.51 | 76.98 | 68.58 | 0.89 |
| 9 | 22.55 | 54.33 | 2.41 | 65.02 | 47.53 | 0.73 |
| 10 | 21.79 | 13.06 | 0.60 | 8.14 | 5.80 | 0.71 |
| 11 | 5.86 | 13.47 | 2.30 | −0.56 | −0.79 | NA |
| 12 | 3.63 | 6.53 | 1.80 | 21.79 | 16.34 | 0.75 |
| 13 | 28.62 | 28.77 | 1.01 | 30.58 | 22.52 | 0.74 |
| 14 | 2.67 | 10.52 | 3.93 | 28.26 | 19.16 | 0.68 |
| 15 | 0.43 | 0.51 | NA | 8.10 | 5.71 | 0.71 |
| 16 | 39.90 | 118.11 | 2.96 | 2.75 | 1.88 | NA |
| 17 | 7.57 | 4.47 | 0.59 | 6.14 | 3.55 | 0.58 |
| 18 | 1.77 | 1.91 | NA | 14.05 | 9.07 | 0.65 |
| 19 | 2.59 | 5.63 | 2.17 | 2.46 | 7.91 | 3.22 |
| 20 | 0.68 | 0.27 | NA | 11.80 | 8.73 | 0.74 |
| | | Mean fold increase | 2.02 | | Mean fold increase | 0.73 |

NA Not applicable as IFN-γ detected was less than 2 IU/mL for either 24-well plate or tube.
*Concentration of IFN-γ in IU/mL after subtraction of the value of the respective saline negative control.
+Mean result from duplicate tubes.

Table 7 shows the ELISA optical density values (450/620 nm) for the saline control samples from both the 24-well and in-tube incubations. The data show that there was no increase in the negative control values when blood was incubated in the blood collection tubes. Therefore, as there is an increase in the amount of IFN-γ produced in response to HuPPD and no increase in background IFN-γ responses, the signal to noise ratio for the in-tube incubation is significantly higher than that seen for the standard 24-well incubation method.

TABLE 7

Background of IFN-γ responses (OD @ 450/620 nm) from 1 mL blood samples incubated with saline in either a 24-well tissue culture plate or a L blood collection tube and tested using the Quantiferon-TB [registered trade mark] ELISA

| Donor | 24-well | Tube A | Tube B | Tube Mean | 24-well Tube Mean |
|---|---|---|---|---|---|
| 1 | 0.024 | 0.023 | 0.027 | 0.025 | −0.001 |
| 2 | 0.02 | 0.02 | 0.023 | 0.022 | −0.002 |
| 3 | 0.033 | 0.024 | 0.025 | 0.025 | 0.009 |
| 4 | 0.026 | 0.026 | 0.023 | 0.025 | 0.002 |
| 5 | 0.021 | 0.021 | 0.022 | 0.022 | 0.000 |
| 6 | 0.069 | 0.063 | 0.060 | 0.062 | 0.008 |
| 7 | 0.024 | 0.022 | 0.023 | 0.023 | 0.002 |
| 8 | 0.023 | 0.025 | 0.039 | 0.032 | −0.009 |
| 9 | 0.021 | 0.021 | 0.021 | 0.021 | 0.000 |
| 10 | 0.021 | 0.024 | 0.021 | 0.023 | −0.002 |
| 11 | 0.022 | 0.026 | ND | 0.026 | −0.004 |
| 12 | 0.023 | 0.024 | 0.022 | 0.023 | 0.000 |
| 13 | 0.017 | 0.018 | 0.017 | 0.018 | −0.001 |
| 14 | 0.018 | 0.021 | 0.021 | 0.021 | −0.003 |
| 15 | 0.019 | 0.020 | ND | 0.020 | −0.001 |
| 16 | 0.017 | 0.016 | 0.021 | 0.019 | −0.002 |
| 17 | 0.017 | 0.015 | 0.016 | 0.016 | 0.002 |
| 18 | 0.02 | 0.018 | 0.018 | 0.018 | 0.002 |
| 19 | 0.02 | 0.019 | 0.021 | 0.020 | 0.000 |
| 20 | 0.018 | 0.020 | 0.018 | 0.019 | −0.001 |
| | | Mean OD for 24-well minus tube | | | 0.000 |

EXAMPLE 5

Effect of Incubation of Blood with Tetanus Toxoid in Blood Collection Tubes, with and without Dextrose Twenty heparinized blood samples were collected from blood bank donors and 3×1 mL aliquots were dispensed into individual wells of a 24-well tissue culture tray. To the respective wells, 125 μL of Saline, Tetanus toxoid, or Tetanus toxoid+dextrose were added. After mixing, the culture trays were incubated for 20 hours at 37° C. in a humidified atmosphere, before harvesting of plasma samples.

One mL aliquots of blood were also added to duplicate Vacuette [registered trade mark] tubes (Greiner Bio-one, Germany), which had previously had the same antigens as above added. The capped tubes were then mixed for 20 seconds using a vortex mixer and incubated for 20 hours at 37° C., before harvesting of plasma samples.

Samples from blood that had been stimulated with the saline control, tetanus toxoid, and tetanus toxoid with dextrose were tested using the sensitive Quantiferon-CMI ELISA which has a threshold of detection of 0.05 IU/mL. The results demonstrate that an average 4.5-fold increase in the amount of IFN-γ detected, above that for the saline control, was found for blood that had been incubated with tetanus toxoid in the blood collection tubes, as compared with the 24-well tissue culture tray (Table 8). Moreover, results from the tubes containing tetanus toxoid and dextrose demonstrated a greater than 7.8-fold increase in IFN-γ production over the 24-well tray (Table 8).

TABLE 8

Amount of IFN-γ detected (IU/mL) from 1 mL blood samples incubated with tetanus toxoid with or without dextrose added in either a 24-well tissue culture plate or a blood collection tube

| Donor | 24-well | Tube | Tube + Dextrose | TetTox Tube/24 well | TetTox + Dextrose Tube/24 well |
|---|---|---|---|---|---|
| 1 | 1.58 | 1.34 | 7.15 | 0.85 | 4.53 |
| 2 | 12.345 | 22.15 | 23.29 | 1.79 | 1.89 |
| 3 | 0.118 | 0.38 | 0.55 | 3.22 | 4.64 |
| 4 | 0.406 | 4.20 | 3.04 | 10.34 | 7.50 |
| 5 | 0.38 | 2.85 | 5.26 | 7.50 | 13.84 |
| 6 | 13.66 | 17.96 | 20.80 | 1.31 | 1.52 |
| 7 | 0.406 | 1.86 | 1.98 | 4.59 | 4.87 |
| 8 | 0.337 | 1.10 | 3.25 | 3.26 | 9.65 |
| 9 | 26.488 | 29.92 | 28.69 | 1.13 | 1.08 |
| 10 | 0.074 | 0.10 | 0.35 | 1.28 | 4.68 |
| 11 | 0.015 | 0.11 | 0.09 | 7.40 | 5.67 |
| 12 | 0.843 | 4.43 | 12.56 | 5.26 | 14.90 |
| 13 | 1.703 | 9.15 | 20.91 | 5.37 | 12.28 |
| 14 | 0.777 | 6.46 | 3.45 | 8.31 | 4.44 |
| 15 | 0.258 | 2.31 | 8.75 | 8.96 | 33.92 |
| 16 | 5.528 | 28.08 | 27.13 | 5.08 | 4.91 |
| 17 | 0.092 | 0.09 | 0.18 | 1.00 | 1.94 |
| 18 | 0.323 | 2.05 | 5.14 | 6.35 | 15.92 |
| 19 | 4.162 | 28.39 | 29.22 | 6.82 | 7.02 |
| 20 | 3.587 | 1.54 | 5.50 | 0.43 | 1.53 |
| Mean fold increase | | | | 4.51 | 7.84 |

Table 9 shows the amount of IFN-γ detected (IU/mL) for the saline control samples from both the 24-well and in-tube incubations when tested using the sensitive IFN-γ ELISA. The data shows that there was a slight decrease in the negative control values when blood was incubated in the blood collection tubes. Therefore, as there is an increase in the amount of IFN-γ produced in response to tetanus toxoid and a slight decrease in background IFN-γ responses, the signal to noise ratio for the in-tube incubation is significantly higher than that seen for the standard 24-well incubation method.

TABLE 9

Background IFN-γ responses (IU/mL) from 1 mL blood samples incubated with saline in either a 24-well tissue culture plate or a blood collection tube and tested using a sensitive IFN-γ ELISA

| Donor | 24-well | Tube A | Tube B | Tube Mean | 24-well − Tube Mean |
|---|---|---|---|---|---|
| 1 | 0.166 | 0.137 | 0.137 | 0.137 | 0.029 |
| 2 | 0.039 | 0.038 | 0.028 | 0.033 | 0.006 |
| 3 | 0.044 | 0.010 | 0.016 | 0.013 | 0.031 |
| 4 | 0.030 | 0.025 | 0.028 | 0.027 | 0.004 |
| 5 | 0.029 | 0.024 | 0.024 | 0.024 | 0.005 |
| 6 | 0.571 | 0.539 | 0.568 | 0.554 | 0.018 |
| 7 | 0.030 | 0.029 | 0.029 | 0.029 | 0.001 |
| 8 | 0.044 | 0.020 | 0.017 | 0.019 | 0.026 |
| 9 | 0.085 | 0.067 | 0.067 | 0.067 | 0.018 |
| 10 | 0.041 | 0.030 | 0.032 | 0.031 | 0.010 |
| 11 | 0.026 | 0.030 | ND | 0.026 | 0.000 |
| 12 | 0.024 | 0.026 | 0.022 | 0.024 | 0.000 |
| 13 | 0.043 | 0.032 | 0.032 | 0.032 | 0.011 |
| 14 | 0.036 | 0.032 | 0.036 | 0.034 | 0.002 |
| 15 | 0.034 | 0.030 | ND | 0.015 | 0.019 |
| 16 | 0.045 | 0.034 | 0.038 | 0.036 | 0.009 |
| 17 | 0.043 | 0.034 | 0.036 | 0.035 | 0.008 |
| 18 | 0.038 | 0.043 | 0.043 | 0.043 | −0.005 |
| 19 | 0.045 | 0.031 | 0.027 | 0.029 | 0.016 |
| 20 | 0.074 | 0.029 | 0.036 | 0.033 | 0.042 |
| Mean OD for 24-well minus tube | | | | | 0.012 |

To test the effect of adding dextrose to the saline negative control blood incubation wells, blood from 9 of the 20 donors was cultured with the saline control and with and without dextrose in 24-well plates. The data show that there was no significant difference in background levels of IFN-γ detected when dextrose was added to the saline control stimulated blood samples (Table 10).

TABLE 10

Background IFN-γ responses (OD @ 450/620 nM) from blood samples incubated with saline in 24-well tissue culture plates with or without dextrose and tested using a using a sensitive IFN-γ ELISA

| Donor | 24-well | 24-well + Dextrose |
|---|---|---|
| 2 | 0.035 | 0.036 |
| 7 | 0.029 | 0.028 |
| 12 | 0.016 | 0.019 |
| 13 | 0.025 | 0.022 |
| 14 | 0.022 | 0.021 |
| 16 | 0.026 | 0.032 |
| 17 | 0.024 | 0.017 |
| 19 | 0.025 | 0.019 |
| 20 | 0.036 | 0.025 |

EXAMPLE 6

Comparison of In-Tube vs Culture Plate Simulation

The assay of the present invention quantifies IFN-γ generated as a CMI response to the stimulation of whole blood with test antigens. Stimulation of 1 mL volumes of blood with a panel of negative control (Nil), positive control (Mitogen) and test antigens is performed in a 24-well culture plate.

The "In-Tube" stimulation culture method is an alternate technology developed for use in the assay system. This method employs the addition of either Nil, Mitogen or test stimulation antigens to heparinized blood collection tubes for the purpose of initiating blood stimulation immediately upon the drawing of a 1 mL blood sample. Dextrose is also added to the tubes in order to enhance IFN-γ response.

This experiment aimed to compare the two blood culture methods, the culture plate versus the in-tube.

Heparinized blood from patients diagnosed with Tuberculosis was stimulated in 24-well culture plate (Corning-Costar) with Nil (negative control), Mitogen (phytohaemaglutti-nin; positive control) and TB-specific antigens (overlapping peptides for ESAT-6, CFP-10 and a 25 mer section of TB7.7). Blood was also collected into 3 blood collection tubes (Greiner) with the same Nil, PHA, and TB-specific antigens in the tubes, along with heparin. The blood samples were incubated for 16 to 24 hours at 37° C. before harvesting plasma from above the settled blood cells. Plasma samples were tested to determine the IFN-γ concentration using ELISA and in some cases TB ELISA (if the specific antigen response was >15 IU/mL).

The culture plate and in-tube results from 10 patents were compared. Nil values were substracted from each of the TB-Specific Antigen responses. The patent's "Mitogen minus Nil" result of "Specific Antigen minus Nil" result had to be >0.5 IU/mL for the data to be considered valid (as per the product insert for TB ELISA). The results are shown in Table 11.

TABLE 11

Comparison of Culture Plate and Blood Collection Tube (In-Tube) whole blood stimulation

| | Culture Plate Method | | | In-Tube Method | | | Culture Plate Specific Antigens – Nil | In-Tube Specific Antigens – Nil | Fold Change of Specific antigen (In-Tube vs Plate) |
|---|---|---|---|---|---|---|---|---|---|
| Subject | Nil | Specific Antigens | Mitogen | Nil | Specific Antigens | Mitogen | | | |
| 1 | 0.18 | 282.90 | 128.70 | 1.30 | 424.90 | 52.50 | 282.72 | 423.60 | 1.50 |
| 2 | 0.10 | 2.46 | 15.182* | 0.29 | 7.55 | 4.15 | 2.36 | 7.27 | 3.08 |
| 3 | 0.12 | 1.01 | 17.017* | 0.20 | 5.51 | 17.377* | 0.89 | 5.31 | 5.99 |
| 4 | 0.09 | 2.72 | 6.52 | 0.08 | 5.95 | 5.57 | 2.64 | 5.88 | 2.23 |
| 5 | 0.07 | 2.96 | 8.25 | 0.06 | 3.89 | 2.31 | 2.89 | 3.83 | 1.32 |
| 6 | 0.07 | 5.04 | 19.76* | 0.09 | 10.31 | 11.77 | 4.98 | 10.21 | 2.05 |
| 7 | 0.30 | 1.34 | 19.868* | 0.46 | 4.14 | 21.063* | 1.05 | 3.68 | 3.52 |
| 8 | 1.22 | 2.05 | 11.11 | 0.61 | 1.81 | 4.02 | 0.83 | 1.21 | 1.44 |
| 9 | 0.09 | 1.22 | 14.66 | 0.16 | 2.17 | 11.23 | 1.13 | 2.01 | 1.78 |
| 10 | 0.11 | 4.26 | 12.65 | 0.62 | 9.27 | 17.05* | 4.15 | 8.65 | 2.08 |
| | | | | | | | | Mean | 2.50 |

*OD outside the range of the plate reader

The data indicate that an increased IFN-γ response is obtained using the In-Tube system compared to the current culture plate method (mean fold change=2.50).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPY

Biggs et al., *Cytometry* 36: 36-45, 1999.
Daneshvar et al., *J. Immunol. Methods* 226(1-2): 119-128, 1999.
Durig et al., *J. Raman Spectrosc.* 24(5): 281-285, 1993.
Eriksson et al., *Biophys. J.* 2: 64, 1993.
Fu et al., *Nature Biotechnology* 17: 1109-1111, 1999.
Lakowicz et al., *Biophys. J.* 72: 567, 1997.
Lewis et al., *Dyes Pigm.* 42(2): 197, 1999.
Malemed et al., "*Flow cytometry and sorting*", 2$^{nd}$ Ed., New York, Wiley-Liss, 1990).
Rahman et al., *J. Org. Chem.* 63: 6196, 1998.
Rapaport et al., *Appl. Phys. Lett.* 74(3): 329-331, 1999.
Tawa et al., *Mater. Res. Soc. Symp. Proc.* 488 [Electrical, Optical and Magnetic Properties of Organic Solid-State Materials IV], 885-890.
Youvan et al., *Biotechnology et elia* 3: 1-18, 1997.

The invention claimed is:

1. A method for measuring a CMI response in a subject, said method comprising;
    collecting a whole blood sample from said subject wherein said whole blood sample comprises cells of the immune system which are capable of producing immune effector molecules following stimulation by an antigen,
    incubating a mixture comprising the whole blood sample, the antigen and an amount of an isolated simple sugar effective to enhance the stimulation by the antigen, and optionally heparin, and
    measuring the presence of, or elevation in, the level of an immune effector molecule wherein the presence or level of said immune effector molecule is indicative of the capacity of said subject to mount a cell-mediated immune response.

2. The method of claim 1 wherein the subject is a human.

3. The method of claim 1 wherein the whole blood is collected in a tube comprising antigen.

4. The method of claim 1 wherein the whole blood is collected in a tube comprising heparin.

5. The method of claim 3 wherein the tube comprises heparin.

6. The method of claim 1 wherein the whole blood sample is incubated with the antigen for from about 5 to about 50 hours.

7. The method of claim 1 wherein the immune effector molecule is a cytokine.

8. The method of claim 7 wherein the cytokine is IFN-γ.

9. The method of claim 7 wherein the cytokine is GM-CSF.

10. The method of claim 7 wherein the cytokine is an interleukin.

11. The method of claim 7 wherein the cytokine is a TNF-α.

12. The method of claim 1 or 2 wherein the subject is infected by a pathogenic agent.

13. The method of claim 12 wherein the pathogenic agent is HBV.

14. The method of claim 12 wherein the pathogenic agent is HIV.

15. The method of claim 1 wherein the immune cells are selected from NK cells, T-cells, B-cells, dendritic cells, macrophages or monocytes.

16. The method of claim 15 wherein the immune cells are T-cells.

17. The method of claim 1 wherein the simple sugar is dextrose.

18. The method of claim 1 wherein the antigen is a peptide.

19. The method of claim 1 wherein the antigen is a polypeptide.

20. The method of claim 1 wherein the antigen is a protein.

21. The method of claim 1 wherein the antigen is a glycoprotein.

22. The method of claim 1 wherein the antigen is a carbohydrate.

23. The method of claim 1 wherein the antigen is selected from a phospholipid, phosphoprotein and a phospholipoprotein.

24. The method of claim 1 wherein the antigen is a TB-specific antigen.

25. The method of claim 24 wherein the TB-specific antigen is ESAT-6.

26. The method of claim 24 wherein the TB-specific antigen is CFP-10.

27. The method of claim 24 wherein the TB-specific antigen is TB7.

28. The method of claim 1 wherein the antigen is PPD from *Mycobacterium tuberculosis*.

29. The method of claim 1 wherein the antigen is PPD from *Mycobacteriun avium*.

30. The method of claim 1 wherein the antigen is tetanus toxoid.

31. The method of claim 1 wherein the immune effectors are detected with antibodies specific for same.

32. The method of claim 31 wherein the immune effectors are detected using ELISA.

33. The method of claim 31 wherein the immune effectors are detected using ELISpot.

34. A method of treatment of a subject having a pathogenic infection, an autoimmune disorder or cancer or a propensity for developing such a disorder, said method comprising assessing the ability for said subject to mount a cell mediated immune response by the method of measuring a CMI response in a subject, said method of measuring comprising,
collecting a whole blood sample from said subject wherein said whole blood sample comprises cells of the immune system which are capable of producing immune effector molecules following stimulation by an antigen,
incubating a mixture comprising the whole blood sample, antigen and an amount of an isolated simple sugar effective to enhance the stimulation by the antigen, and optionally heparin, and
measuring the presence of or elevation in the level of an immune effector molecule wherein the presence or level of said immune effector molecule is indicative of the capacity of said subject to mount a cell-mediated immune response and
selecting a suitable therapeutic protocol.

35. The method of claim 34 wherein the subject is a human.

36. The method of claim 34 wherein the whole blood is collected in a tube comprising antigen.

37. The method of claim 34 wherein the whole blood is collected in a tube comprising heparin.

38. The method of claim 36 wherein the tube comprises heparin.

39. The method of claim 34 wherein the whole blood sample is incubated with the antigen for from about 5 to about 50 hours.

40. The method of claim 34 wherein the immune effector molecule is a cytokine.

41. The method of claim 40 wherein the cytokine is IFN-γ.

42. The method of claim 40 wherein the cytokine is GM-CSF.

43. The method of claim 40 wherein the cytokine is an interleukin.

44. The method of claim 40 wherein the cytokine is a TNF-α.

45. The method of claim 34 wherein the immune cells are selected from NK cells, T-cells, B-cells, dendritic cells, macrophages or monocytes.

46. The method of claim 45 wherein the immune cells are T-cells.

47. The method of claim 34 wherein the simple sugar is dextrose.

48. The method of claim 34 wherein the antigen is selected from a peptide.

49. The method of claim 34 wherein the antigen is selected from a polypeptide.

50. The method of claim 34 wherein the antigen is selected from a protein.

51. The method of claim 34 wherein the antigen is selected from a glycoprotein.

52. The method of claim 34 wherein the antigen is selected from a carbohydrate.

53. The method of claim 34 wherein the antigen is selected from a phospholipid, phosphoprotein and phospholipoprotein.

54. The method of claim 34 wherein the antigen is a TB-specific antigen.

55. The method of claim 54 wherein the TB-specific antigen is ESAT-6.

56. The method of claim 54 wherein the TB-specific antigen is CFP-10.

57. The method of claim 54 wherein the TB-specific antigen is TB-7.

58. The method of claim 34 wherein the antigen is PPD from *Mycobacterium tuberculosis*.

59. The method of claim 34 wherein the antigen is PPD for *Mycobacterium avium*.

60. The method of claim 34 wherein the antigen is phytohemagglutinin.

61. The method of claim 34 wherein the antigen is tetanus toxoid.

62. The method of claim 34 wherein the immune effectors are detected with antibodies specific for same.

63. The method of claim 62 wherein the immune effectors are detected using ELISA.

64. The method of claim 63 wherein the immune effectors are detected using ELISpot.

* * * * *

UNITED STATES PATENT AND TRADEMARK OFFICE
CERTIFICATE OF CORRECTION

PATENT NO.        : 7,608,392 B2                                   Page 1 of 1
APPLICATION NO.   : 10/477571
DATED             : October 27, 2009
INVENTOR(S)       : Rothel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 625 days.

Signed and Sealed this

Twelfth Day of October, 2010

David J. Kappos
*Director of the United States Patent and Trademark Office*